(12) United States Patent
Norton et al.

(10) Patent No.: US 9,073,649 B2
(45) Date of Patent: Jul. 7, 2015

(54) FINGER GRIP FOR A FLANGELESS CONTAINER

(75) Inventors: Paul H. Norton, Trumbauersville, PA (US); Edward Vander Bush, Hershey, PA (US); Scott Young, Kennett Square, PA (US); Bernard Lahendro, Gallatin Gateway, MT (US)

(73) Assignee: West Pharmaceutical Services, Inc., Exton, PA (US)

( * ) Notice: Subject to any disclaimer, the term of this patent is extended or adjusted under 35 U.S.C. 154(b) by 0 days.

(21) Appl. No.: 13/387,464

(22) PCT Filed: Aug. 6, 2010

(86) PCT No.: PCT/US2010/044712
§ 371 (c)(1),
(2), (4) Date: Jan. 27, 2012

(87) PCT Pub. No.: WO2011/019605
PCT Pub. Date: Feb. 17, 2011

(65) Prior Publication Data
US 2012/0118903 A1  May 17, 2012

Related U.S. Application Data

(60) Provisional application No. 61/232,691, filed on Aug. 10, 2009.

(51) Int. Cl.
*A61M 5/34* (2006.01)
*B65B 3/00* (2006.01)
(Continued)

(52) U.S. Cl.
CPC ............... *B65B 3/003* (2013.01); *A61M 5/344* (2013.01); *A61M 5/3137* (2013.01); *B01L 3/0293* (2013.01); *B01L 9/06* (2013.01); *B65B 7/2821* (2013.01)

(58) Field of Classification Search
CPC ...... A61M 5/344; A61M 5/345; A61M 5/346; A61M 5/347; A61M 5/348; A61M 5/349; A61M 5/3129; A61M 5/3134; A61M 5/3135; A61M 5/3137; A61M 2005/3139
USPC ........................... 220/755; 604/227, 187, 110
See application file for complete search history.

(56) References Cited

U.S. PATENT DOCUMENTS 1,832,533 A * 11/1931 Creasy .......................... 604/227
2,047,512 A *  7/1936 Kauffman .................... 604/227
(Continued)

FOREIGN PATENT DOCUMENTS

DE   102006005784 A1   8/2006
EP       0719712 A1   7/1996
(Continued)

OTHER PUBLICATIONS
International Search Report & Written Opinion mailed Apr. 19, 2011 for PCT/US2010/044712, 14 pgs.
(Continued)

*Primary Examiner* — Anthony Stashick
*Assistant Examiner* — Ernesto Grano
(74) *Attorney, Agent, or Firm* — Panitch Schwarze Belisario & Nadel LLP

(57) ABSTRACT

A finger grip for a flangeless container, the finger grip having a skirt removably attachable to an open end portion of the container and a lip that extends radially outwardly from the skirt. The flangeless container is fillable by capping the container using a cap element to attach the finger grip to the container; installing the container in a container support assembly including a tray having a plurality of wells; filling the container; inserting a piston into the container; and removing the finger grip. Each well has a depth less than a predetermined length of the container, a lower portion of each well having a first cross-sectional shape similar to but greater than the cross-sectional shape of the flangeless container, an upper portion of each well having a second cross-sectional shape similar to but greater than the first cross-sectional shape.

4 Claims, 12 Drawing Sheets

(51) Int. Cl.
  *B01L 3/02* (2006.01)
  *B01L 9/06* (2006.01)
  *B65B 7/28* (2006.01)
  *A61M 5/31* (2006.01)

(56) References Cited

U.S. PATENT DOCUMENTS

| | | | |
|---|---|---|---|
| 2,678,647 A * | 5/1954 | Bruger | 604/227 |
| 3,245,194 A | 4/1966 | Carski | |
| 3,534,989 A * | 10/1970 | Yonkers | 403/369 |
| 3,921,633 A * | 11/1975 | Tischlinger | 604/227 |
| 3,978,858 A | 9/1976 | Tischlinger | |
| 4,729,208 A | 3/1988 | Galy et al. | |
| 4,863,023 A | 9/1989 | Payne et al. | |
| 5,147,305 A * | 9/1992 | Nakamura et al. | 604/110 |
| 5,338,309 A * | 8/1994 | Imbert | 604/187 |
| 5,342,581 A | 8/1994 | Sanadi | |
| 5,419,775 A * | 5/1995 | Haffner et al. | 604/227 |
| 5,607,399 A * | 3/1997 | Grimard et al. | 604/220 |
| 5,700,247 A | 12/1997 | Grimard et al. | |
| 5,782,815 A * | 7/1998 | Yanai et al. | 604/218 |
| 5,833,669 A * | 11/1998 | Wyrick | 604/234 |
| 5,836,919 A * | 11/1998 | Skurka et al. | 604/187 |
| 5,897,532 A * | 4/1999 | Spallek et al. | 604/187 |
| 6,159,184 A * | 12/2000 | Perez et al. | 604/192 |
| 6,296,625 B1 * | 10/2001 | Vetter et al. | 604/227 |
| 6,640,842 B1 | 11/2003 | Laukenmann et al. | |
| 7,757,879 B2 * | 7/2010 | Schuetz et al. | 220/258.2 |
| D649,632 S * | 11/2011 | Morgan et al. | D24/127 |
| 2009/0036839 A1 | 2/2009 | Phalen | |

FOREIGN PATENT DOCUMENTS

| | | |
|---|---|---|
| EP | 0976453 A2 | 2/2000 |
| FR | 2498933 A1 | 8/1982 |
| WO | 2009015862 A1 | 2/2009 |

OTHER PUBLICATIONS

Int'l Preliminary Report on Patentability issued Feb. 23, 2012 in Int'l Application No. PCT/US2010/044712.
Office Action issued Nov. 20, 2013 in CN Application No. 201080035782.2.
Office Action issued Oct. 1, 2013 in EP Application No. 10 745 060.3.
Office Action issued Jul. 10, 2014 in CN Application No. 201080035782.2.

* cited by examiner

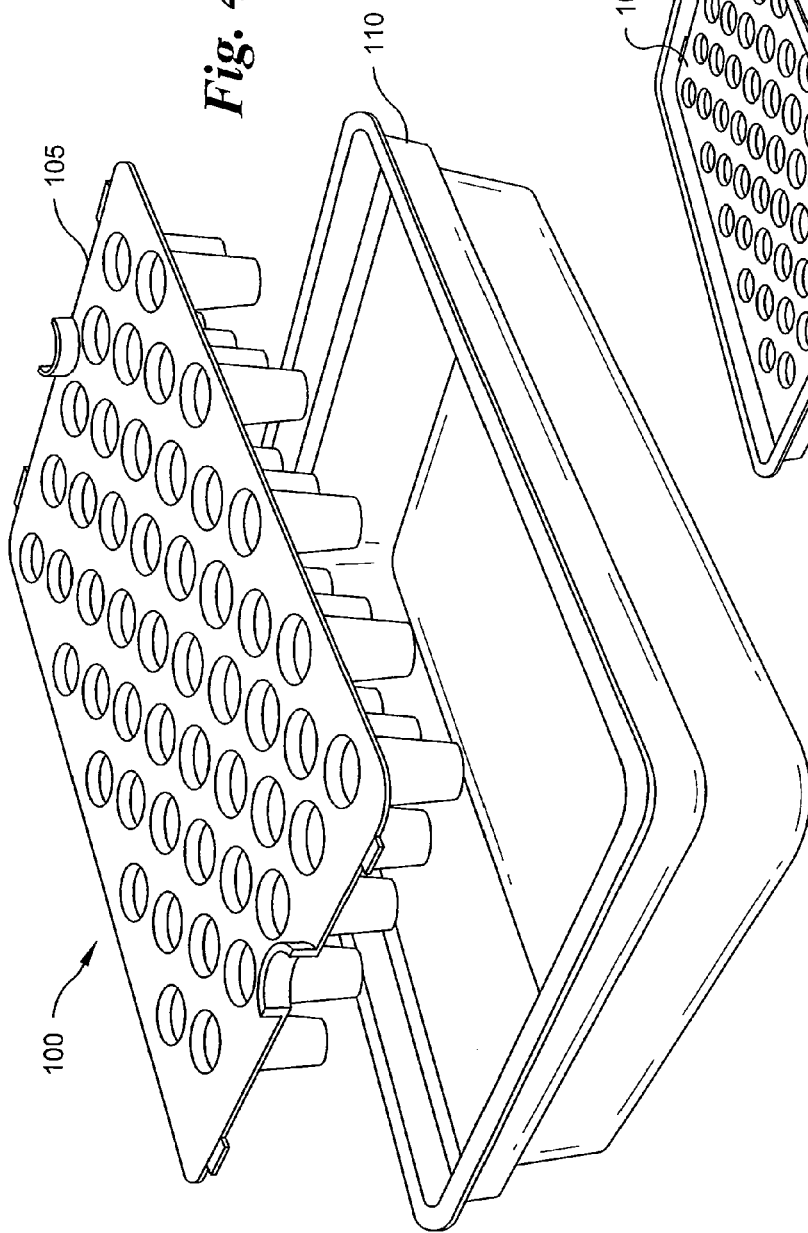
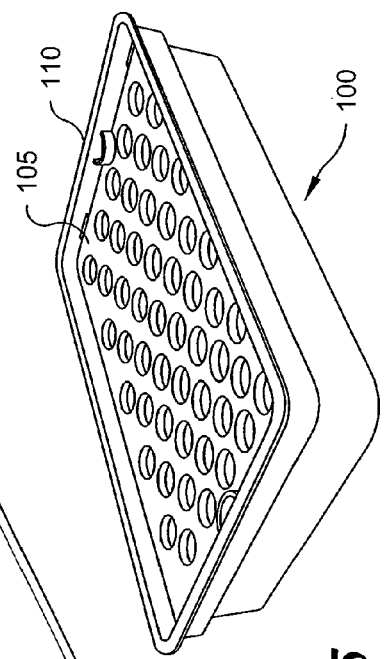

FINGER GRIP FOR A FLANGELESS CONTAINER

CROSS-REFERENCE TO RELATED APPLICATIONS

This application is filed under 35 U.S.C. §371, based on and claiming the benefit of International Patent Application No. PCT/US2010/044712, with an international filing date of Aug. 6, 2010, designating the United States and filed in the English language, which International Patent Application, in turn, claims the benefit of U.S. Provisional Patent Application No. 61-232,691, filed Aug. 10, 2009. Each of the above-identified related applications is incorporated herein by reference.

BACKGROUND OF THE INVENTION

This invention relates to apparatuses and methods for filling flangeless containers, especially pre-filled syringes and drug cartridges.

Pre-filled syringes and drug cartridges are known. In particular, pre-filled syringes having a flange at an open end of the syringe barrel are known. With reference to FIG. 1, a syringe container 10 includes flange 30 disposed at open end 20 of the container 10. During the filling process, a plurality of syringe containers 10 are typically stored in a nest or tray 40, having a planar floor 50. Each individual container 10 is supported by a tubular support 60 extending upwardly from the floor 50. Further, during the filling process a set of containers 10 may be removed from the nest 40 by the engagement of transport rods 70 which can be moved into position underneath the flange 30 to allow the container 10 to be picked up, moved to a filling station, and then moved back into the tray 40. Much of the currently installed filling equipment is designed for use with flanged containers.

Flangeless containers such as pre-filled drug cartridges may be used in auto-injectors. A flange is typically not necessary to support a cartridge used in an auto-injector. Indeed, providing a flange on a cartridge intended for use in an auto-injector may be undesirable, as a conventional flange would require additional and unnecessary space, and undesirably increase the overall physical envelope of the auto-injector.

It would be desirable to provide methods and apparatuses which would allow flangeless drug containers to be filled using conventional filling equipment designed for use with flanged drug containers.

BRIEF SUMMARY OF THE INVENTION

Briefly stated, a first aspect of the present invention is directed to a flangeless container support assembly for receiving flangeless containers having a predetermined length, a predetermined cross-sectional shape and an open end portion with an outer sidewall. The flangeless container support assembly comprises a tray having generally planar floor and a plurality of wells in the floor, each well having a depth less than the predetermined length of the flangeless container, a lower portion of each well having a first cross-sectional shape similar to but greater than the cross-sectional shape of the flangeless container, an upper portion of each well having a second cross-sectional shape similar to but greater than the first cross-sectional shape.

A second aspect of the present invention is directed to a finger grip for a flangeless container having a generally cylindrical cross-sectional shape and an open end portion. The finger grip comprises a skirt having an arcuate cross-sectional shape and a longitudinal extent. The skirt is removably attachable to the open end portion of the container. A lip extends radially outwardly from the skirt.

A third aspect of the present invention is directed to a flangeless container handling apparatus for handling a flangeless container during a filling operation. The flangeless container has an open end portion with an outer sidewall. The handling apparatus comprises a sleeve having a first end, an opposing second end spaced from the first end, and a vacuum port. The first end has a first seal configured to sealably engage the outer sidewall of the open end portion of the container. The second end has a second seal. A knock-out rod has an end portion insertable in the sleeve. A piston is releasably attached to the end portion of the knock-out rod. The piston is configured to sealably engage the open end portion of the container when inserted therein. The first seal cooperates with the second seal to form an airtight seal of an interior of the sleeve when the end portion of the knock-out rod is in the sleeve and a vacuum is applied to the vacuum port. Atmospheric pressure drives the piston out of engagement with the knock-out rod and into a sealing position in the opening of the container when a vacuum applied to the vacuum port is released and the interior of the sleeve is exposed to atmospheric pressure.

A fourth aspect of the present invention is directed to a flangeless container handling apparatus for handling a flangeless container during a filling operation. The flangeless container has an open end with an outer sidewall. The handling apparatus comprises an outer sleeve having a first end, an opposing second end spaced from the first end, the first end having a radially inwardly extending lip. An inner sleeve has a first end movable in the outer sleeve, an opposing second end spaced from the first end, and a vacuum port. The first end of the inner sleeve has a first compression seal. The second end has a second seal. A knock-out rod has an end portion insertable in the inner sleeve. A piston is releasably attached to the end portion of the knock-out rod. The piston is configured to sealably engage the open end of the container when inserted therein. The first compression seal is configured to sealably engage or disengage the outer sidewall of the container and the lip of the outer sleeve in response to an axial movement of the inner and outer sleeves relative to one another and to cooperate with the second seal to form an airtight seal of an interior of the inner sleeve when the end portion of the knock-out rod is in the inner sleeve and a vacuum is applied to the vacuum port. Atmospheric pressure drives the piston out of engagement with the knock-out rod and into a sealing position in the opening of the container when a vacuum applied to the vacuum port is released and the interior of the inner sleeve is exposed to atmospheric pressure.

A fifth aspect of the present invention is directed to a method for filling flangeless containers comprising the steps of: capping the container using a cap element; installing the container in a tray; gripping a sidewall of the container using a handling apparatus to form a seal; filling the container; applying a vacuum to the container; inserting a piston into the container; releasing the vacuum; releasing the piston; and releasing the container from the handling apparatus.

A sixth aspect of the present invention is directed to a method for filling flangeless containers comprising the steps of: capping the container using a cap element; attaching a removable finger grip to the container; installing the container in a tray; filling the container; inserting a piston into the container; and removing the finger grip.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 4 is a perspective view of the tray of FIGS. 2A-3, in combination with a tub adapted to hold the tray;

FIG. 5 is a perspective view of the tray of FIG. 4 installed within the tub of FIG. 4;

DETAILED DESCRIPTION OF THE INVENTION

Figure 1:
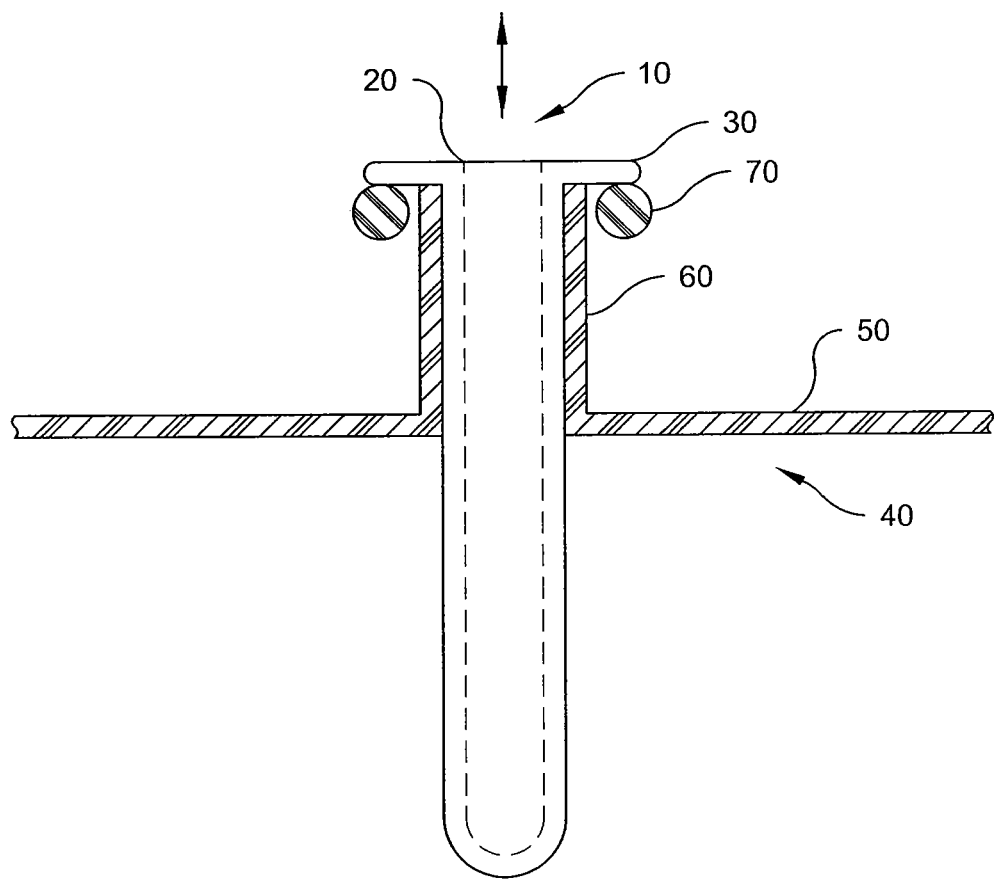
FIG. 1 is a partial cross-sectional side view of a prior art syringe container having a flange positioned in a tray engaged with transport rods, as is known in the prior art.

Certain terminology is used in the following description for convenience only and is not limiting. The words "right", "left", "lower" and "upper" designate directions in the drawings to which reference is made. The words "inwardly" and "outwardly" refer to directions toward and away from, respectively, the geometric center of the sign-stand and designated parts thereof. Unless specifically set forth herein, the terms "a", "an" and "the" are not limited to one element but instead should be read as meaning "at least one". The terminology includes the words noted above, derivatives thereof and words of similar import.

With reference to FIGS. 2A through 5, a flangeless container support assembly 100 in accordance with a first aspect of the invention is shown. The flangeless container support assembly 100 is configured for receiving flangeless containers 120 having a predetermined length, a predetermined cross-sectional shape and an open end portion 121 with an outer sidewall 122. In some embodiments, the container 120 may have an arbitrary geometrical cross-sectional shape such as square, rectangular, or triangular. In other embodiments, the container 120 desirably has an oval cross-sectional shape and preferably a circular cross-sectional shape.

The flangeless container support assembly 100 comprises a tray 105 having a generally planar floor 140. A plurality of wells 130 are provided in the floor of the tray 105. Each well 130 is sized and shaped to receive the container or cartridge 120. Desirably, each well 130 has a depth less than the predetermined length of the container 120 such that the open end portion 121 of each container is accessible. In some embodiments, the open end portion 121 extends above the floor 140. Preferably, the open end portion 121 extends sufficiently above the floor 140 so that a handling apparatus (embodiments of which are described herein below) have ready access to a sidewall 122 of the cartridge 120 proximate the open end 121.

In some embodiments, the lower portion 131 of each well 130 has a first cross-sectional shape similar to but greater than the cross-sectional shape of the flangeless container 120 and has an upper portion 132 with a second cross-sectional shape similar to but greater than the first cross-sectional shape. Preferably, the cross-sectional shape of the container is circular. Accordingly, the lower portion 131 of each well has a first diameter greater than the diameter of the container and the upper portion 132 of each well has a second diameter greater than the first diameter.

The flangeless container support assembly 100 may further comprise a tub 110 within which the tray 105 is may be removably inserted, as illustrated in FIG. 5.

In a second aspect, the invention is directed to various embodiments of a removable finger grip provided with a flange used to facilitate handling of the cartridge 120 during a filling process. With reference again to FIG. 1, during a filling process, it is known in the prior art to handle flanged containers (such as syringes) using transport rods 70 which engage a bottom surface of the flange 30 to pick up and remove one or preferably more containers 10 from a tray 40. Such transport rods 70 typically automatically extend into position underneath the container flange 30, pick up the container 10 and remove it from the tray 40, move the container 10 to a filling station (not shown) and finally return the container 10 back to the tray 40 for transport to additional processing activities. When dealing with flangeless containers, however, it has heretofore been unclear how to apply this existing methodology and existing filling equipment.

With reference to FIGS. 6-16, various embodiments of a removable, temporary finger grip provided with a flange are illustrated. Each embodiment is directed toward providing a removable finger grip with a flange which is attached to a container during a filling process, but is removed after the filling process is complete. The removable finger grip and flange thus permits much of the conventional filling equipment adapted for use with conventional flanged containers to be used for filling of flangeless containers.

Figure 6:
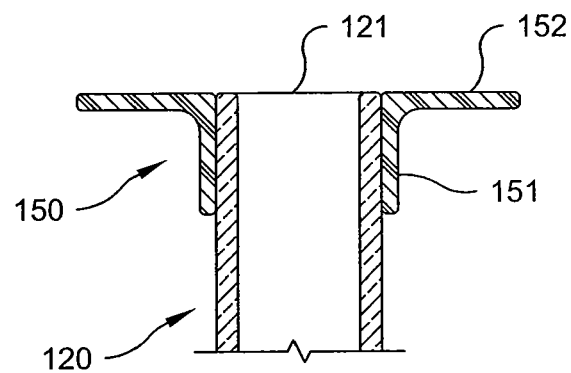
FIG. 6 is a side cross-sectional view of a first embodiment of a removable finger grip in accordance with the present invention.

With particular reference now to FIG. 6, a first embodiment of a removable finger grip 150 is shown attached to a flangeless container 120 having a generally cylindrical cross-sectional shape and an open end portion 121. The finger grip 150 has a skirt 151 having an arcuate cross-sectional shape and a longitudinal extent. The skirt 151 is removably attachable to the open end portion 121 of the container 120. A lip (or flange) 152 extends radially outwardly from the skirt 151. In this embodiment, the skirt 151 has an interference fit with the open end 121. The finger grip 150 can be applied by various methods known in the mechanical arts, such as press fitting the skirt 151 onto the open end 121 of the container 120 or heating the skirt 151 such that it expands, is placed onto the open end 121, and then cools to firmly grip the open end 121. Likewise, once the filling process is complete, the finger grip 15o can be removed by various techniques known in the art, including application of a force sufficient to slide the skirt 151 off of the open end 121, or re-heating the skirt 151 to allow it to expand and be readily removed from the container 120 or cutting the finger grip 150 to allow it to be removed.

Figure 7:
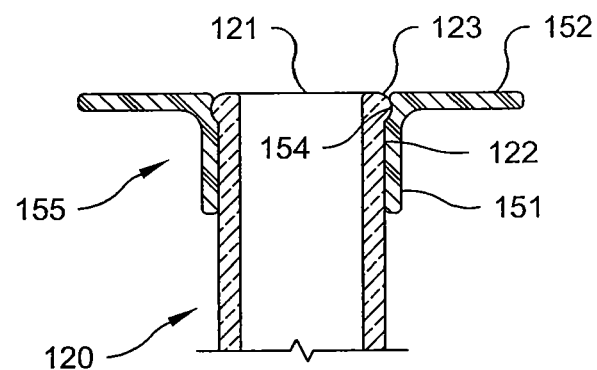
FIG. 7 is a side cross-sectional view of a second embodiment of a removable finger grip in accordance with the present invention.

With particular reference to FIG. 7, a second embodiment of a removable finger grip 155 is shown attached to a flangeless container 120 having a generally cylindrical cross-sectional shape and an open end portion 121 with a "glaze-out" protrusion 123. The finger grip 155 has a skirt 151 having an arcuate cross-sectional shape and a longitudinal extent. A lip (or flange) 152 extends radially outwardly from the skirt 151. The skirt 151 is sized and shaped to circumscribe an outside surface 122 of the open end portion 121 of the container 120 and is removably attachable to the open end portion 121 by a detent 154 on an inside surface 153 of the skirt. The detent 154 is configured to have a releasable interference or snap fit with the glaze-out protrusion 123. The material of the finger grip 155 is chosen to have sufficient flexibility to easily deform to engage and disengage the glaze-out 123 with application of moderate force, such force preferably being applied automatically by a machine.

Figure 9:
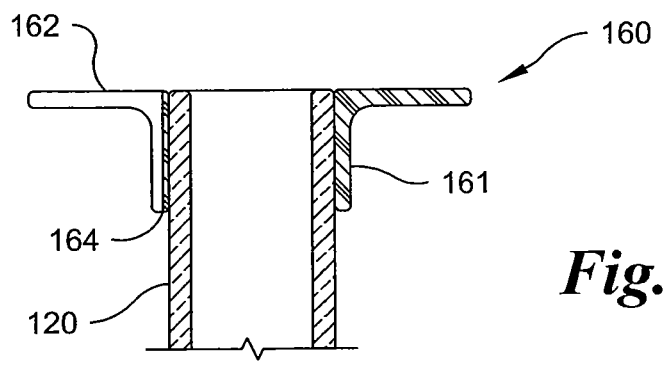
FIG. 9 is a side cross-sectional view of the removable finger grip of FIG. 8B taken along the line 9-9.
Figure 8A:
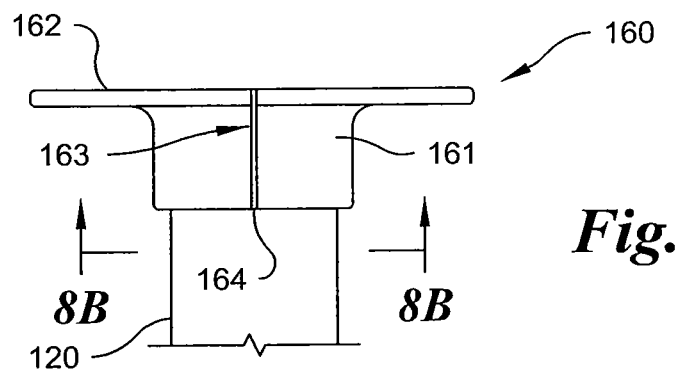
FIG. 8A is a side view of a third embodiment of a removable finger grip in accordance with the present invention.
Figure 8B:
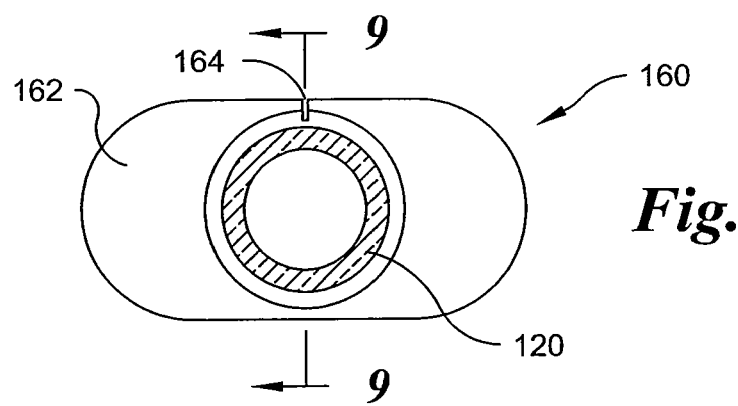
FIG. 8B is a bottom plan view of the removable finger grip of FIG. 8A, taken along line 8B-8B.

With particular reference to FIGS. 8A, 8B, and 9, a third embodiment of a removable finger grip 160 is shown attached to the container 120. The third embodiment finger grip 160 is similar to the first embodiment finger grip 150 described above. In this embodiment, the skirt 161 and lip 162 have an outside surface 163 with a frangible groove 164 or area with a weakened cross-section extending longitudinally. The weakened or frangible area 164 is relatively easily broken after the filling process to remove the finger grip 160 from the container 120.

Figure 10B:
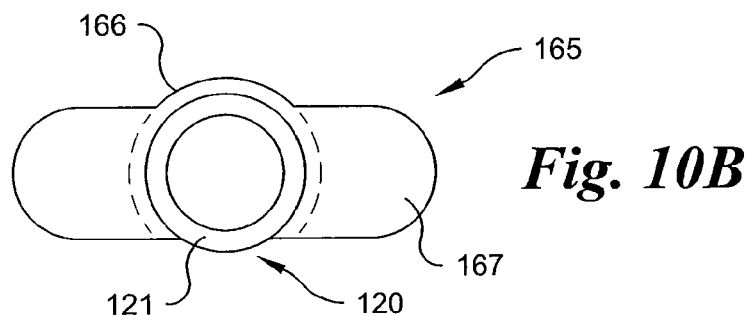
FIG. 10B is a top plan view of the removable finger grip of FIG. 10A.
Figure 10A:
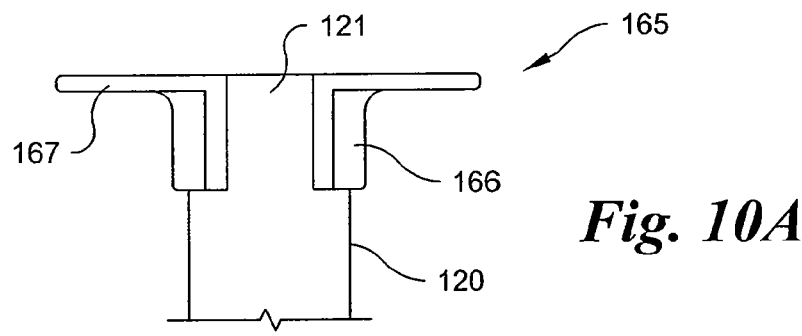
FIG. 10A is a side cross-sectional view of a fourth embodiment of a removable finger grip in accordance with the present invention.

With particular reference now to FIGS. 10A and 10B, a fourth embodiment of a removable finger grip 165 is shown attached to a flangeless container 120 having a generally cylindrical cross-sectional shape and an open end portion 121. The finger grip 165 has a skirt 166 having an arcuate cross-sectional shape and a longitudinal extent. As best shown in FIG. 10B, the skirt extends for more than one hundred eighty degrees circumferentially around an outside surface of the open end portion of the container and is removably attachable to the container by a radial force applied to the skirt. In other words, the finger grip 165 extends only over a portion of a full circumference. That is, the skirt 166 and lip 167 of the finger grip 165 are open along one side of the container 120. As it is not closed circumferentially, the finger grip 165 has increased flexibility, and can be more readily snapped onto the open end 121.

Figure 11:
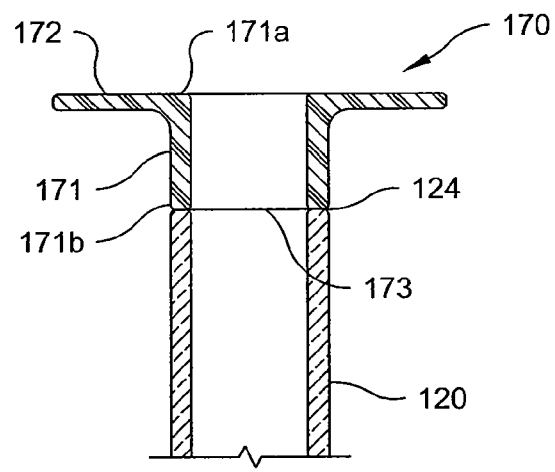
FIG. 11 is a side cross-sectional view of a fifth embodiment of a removable finger grip in accordance with the present invention.

With particular reference now to FIG. 11, a fifth embodiment of a removable finger grip 170 is shown attached to a flangeless container 120 having a generally cylindrical cross-sectional shape and an open end portion 121. The finger grip 170 has a skirt 171 having an arcuate cross-sectional shape and a longitudinal extent. The open end portion 121 of the container 120 terminates with an annular surface 124. A lip 172 is located at a first end 171a of the skirt. A second end 171b of the skirt, spaced from the first end 171a, is attached to the annular surface 124 of the container 120 by a releasable adhesive 173.

Figure 12:
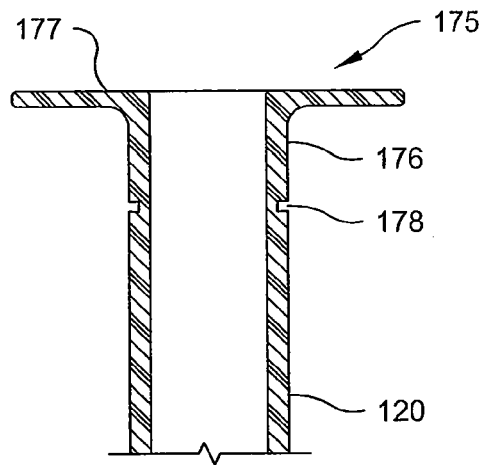
FIG. 12 is a side cross-sectional view of a sixth embodiment of a removable finger grip in accordance with the present invention.

With reference to FIG. 12, a sixth embodiment of a removable finger grip 175 is shown attached to a flangeless container 120 having a generally cylindrical cross-sectional shape and an open end portion 121. The finger grip 175 has a skirt 176 having an arcuate cross-sectional shape and a longitudinal extent. A lip (or flange) 177 extends radially outwardly from the skirt 176. The lip 17, the skirt 176 and the container 120 are formed as a single unitary structure. The container 120 is separable from the skirt 176 by a circumferentially extending frangible connecting area 178 spaced longitudinally from the lip 177. In a plastic embodiment, the frangible connecting area 178 is molded to create a thinned, weakened portion which is readily broken. In a glass embodiment, the frangible connection 178 may be a score line which may be readily broken mechanically or thermally.

Figure 13A:
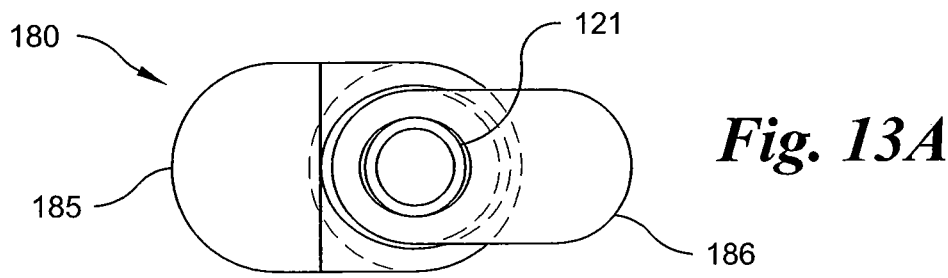
FIG. 13A is a top plan view of a seventh embodiment of a removable finger grip showing the inner sleeve engaging the sidewall of the container in accordance with the present invention.
Figure 13B:
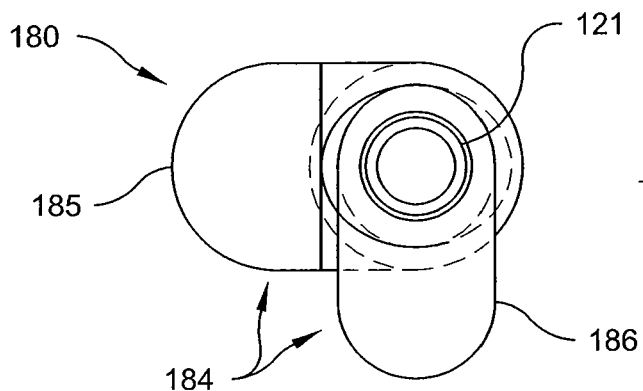
FIG. 13B is a top plan of the removable finger grip of FIG. 13A showing the inner sleeve disengaged from the sidewall of the container.
Figure 13C:
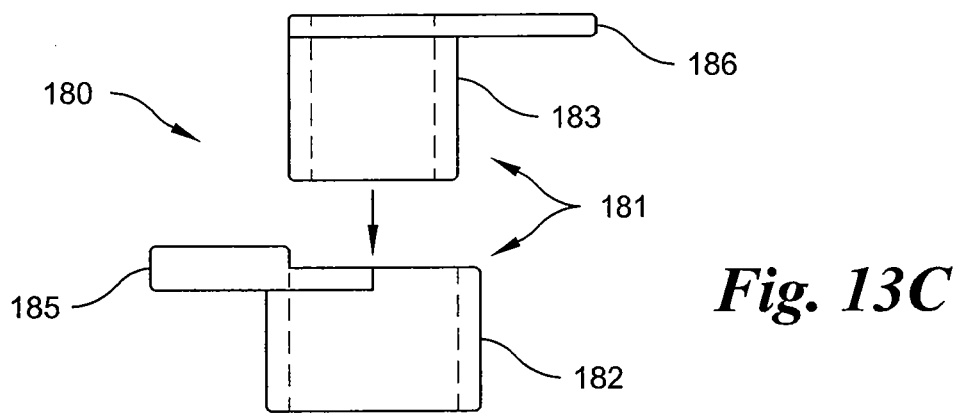
FIG. 13C is a side exploded view of the removable finger grip of FIG. 13A.

With particular reference now to FIG. 13A-13C, a seventh embodiment of a removable finger grip 180 is shown attached to a flangeless container 120 having a generally cylindrical cross-sectional shape and an open end portion 121. The finger grip 180 has a skirt 181 having an arcuate cross-sectional shape and a longitudinal extent. The skirt 181 comprises an outer sleeve 182 with a first elliptical cross-section and an inner sleeve 183 with a second elliptical cross-section in the outer sleeve 182. The lip 184 comprises a first lip portion 185 extending radially outwardly from the outer sleeve 182 and a second lip portion 186 extending radially outwardly from the inner sleeve 183. A rotational movement of the inner and outer sleeves 182, 183 relative to one another about a longitudinal axis causes the inner surface of the inner sleeve to engage or disengage with an interference fit an outside surface of the open end portion 121 of the container 120. With the major axes of each sleeve 182, 183 aligned, the minor axis of the inner sleeve 183 has an interference fit with the container 120. Upon rotation of the outer sleeve 182, such that the minor axis of the outer sleeve 182 is aligned with the major axis of the inner sleeve 183, the outer sleeve 182 acts to flex the inner sleeve 183, deforming the inner sleeve 183 out of engagement with the container 120. Thus, the finger grip 180 can be attached to or removed from the container 120 by rotation of the two sleeves 182, 183 relative to one another.

Figure 14:
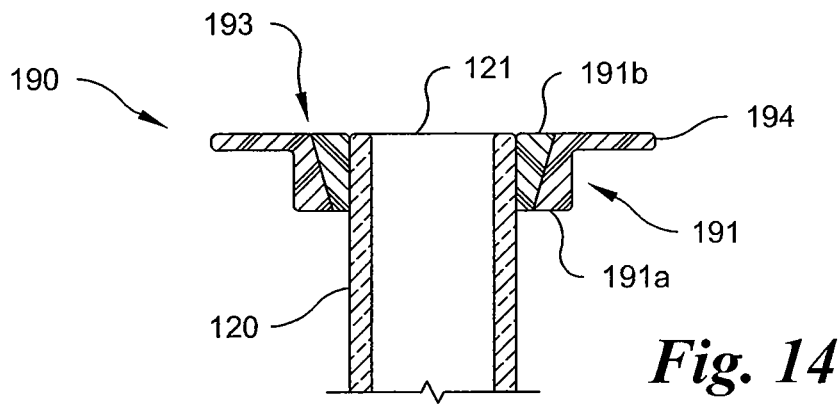
FIG. 14 is a side cross-sectional view of an eighth embodiment of a removable finger grip in accordance with the present invention.
Figure 15:
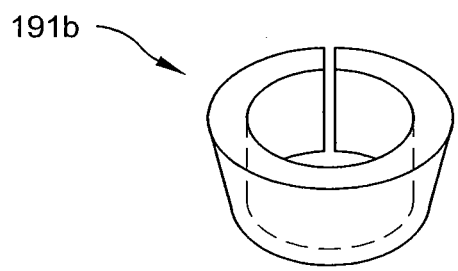
FIG. 15 is a side perspective view of an inner sleeve component of the removable finger grip of FIG. 14.

With particular reference now to FIGS. 14 and 15, an eighth embodiment of a removable finger grip 190 is shown attached to a flangeless container 120 having a generally cylindrical cross-sectional shape and an open end portion 121. The finger grip 190 has a skirt 191 having an arcuate cross-sectional shape and a longitudinal extent. The skirt 191 comprises an outer sleeve 191a and a circumferentially discontinuous, split sleeve 191b in the outer sleeve 191a as illustrated in FIG. 15. The inner surface of the outer sleeve 191a and the outer surface of the inner sleeve 191b having cooperating tapers 193 such that movement of the outer sleeve 191a relative to the inner sleeve 191b in a first axial direction tightens engagement of the inner sleeve 191b with the container and movement of the outer sleeve 191a relative to the inner sleeve 191b in a second axial direction opposite the first axial direction loosens engagement of the inner sleeve 191b with the container 120. The lip 194 extends radially outwardly from the outer sleeve. Thus, by relative axial movement of the inner and outer sleeves 191a, 191b, the eighth embodiment finger grip 190 may be attached to and removed from the flangeless container 120. The finger grip 190 is removed from the container 120 by holding the container 120 and pushing lip 194 of the outer sleeve 191a toward the distal end of the container 120.

Figure 16:
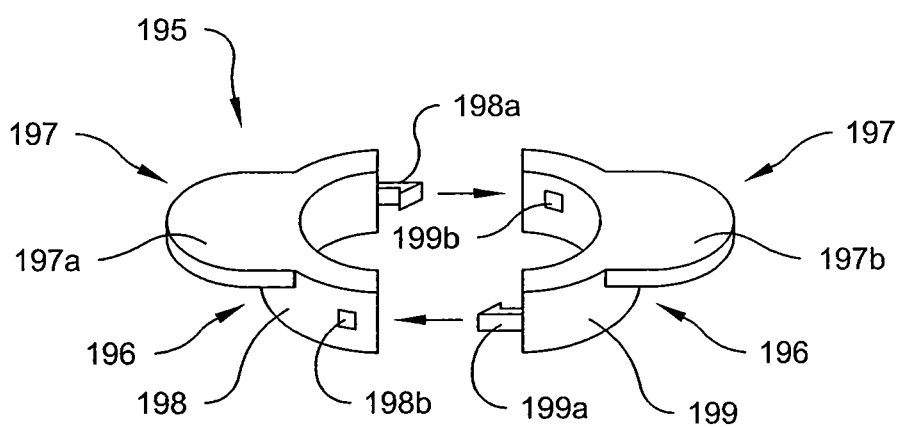
FIG. 16 is a side perspective view of a ninth embodiment of a removable finger grip in accordance with the present invention.

With particular reference now to FIG. 16, a ninth embodiment of a removable finger grip 195 is shown. The finger grip 195 has a skirt 196 and a lip 197. The skirt 196 has an arcuate cross-sectional shape and a longitudinal extent. The skirt 196 comprises a first portion of a sleeve 198 and a second portion of a sleeve 199. The first portion of a sleeve 198 has a first latch 198a and a first recess 198b. The second portion of a sleeve 199 has a second latch 199a and a second recess 199b. The lip 197 comprises a first lip portion 197a extending radially outwardly from the first portion of a sleeve 198 and a second lip portion 197b extending radially outwardly from the second portion of a sleeve 199. The skirt 196 releasably attaches to the container when the first latch 198a releasably engages with the second recess 199b and the first recess 199b releasably engages with the second latch 199a.

Figure 2B:
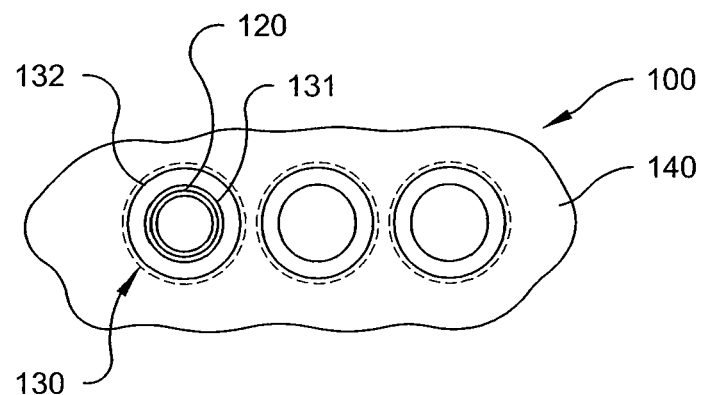
FIG. 2B is a partial top plan view of the tray of FIG. 2A.
Figure 2A:
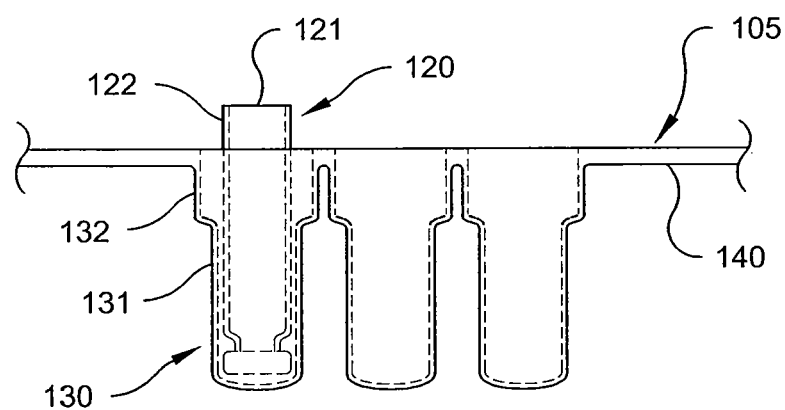
FIG. 2A is a partial side view of a tray in accordance with the present invention.
Figure 3:
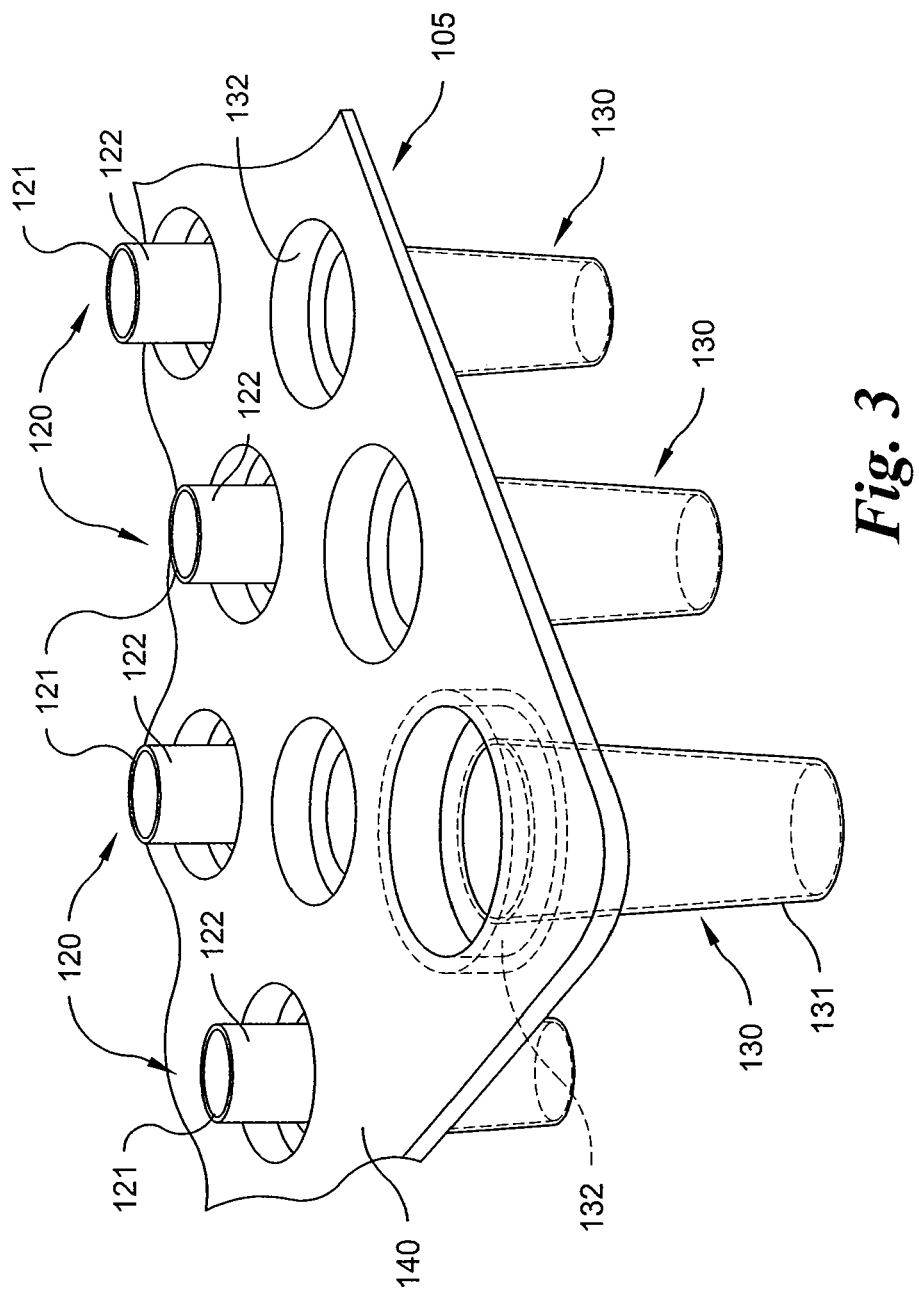
FIG. 3 is a perspective view of a portion of the tray of FIGS. 2A and 2B.
Figure 17:
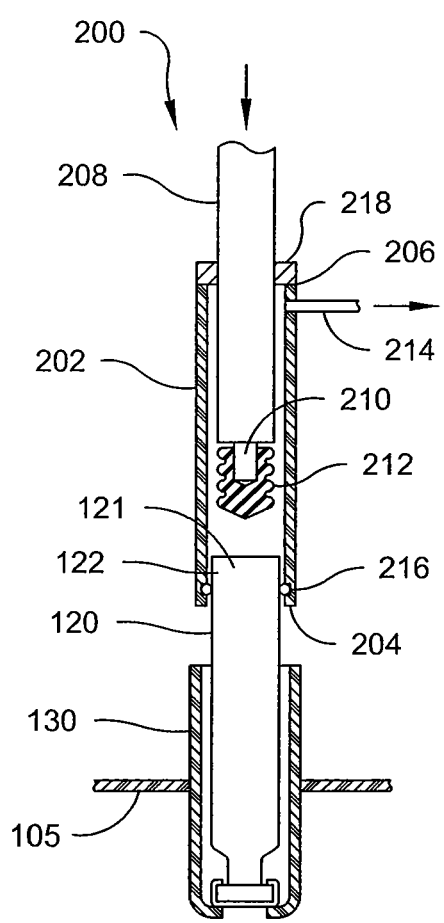
FIG. 17 is a side partial cross-sectional view of a first embodiment of a flangeless container handling apparatus in accordance with the present invention.

Now, in yet a third aspect of the invention, the invention relates to an apparatus for handling flangeless containers during a filling process. With particular reference to FIGS. 2A and 17, a first embodiment of a flangeless container handling apparatus 200 is shown. The handling apparatus 200 is for handling a flangeless container 120 during a filling operation. The flangeless container 120 has an open end portion 121 with an outer sidewall 122. The handling apparatus 200 comprises a sleeve 202 a having a first end 204 and an opposing second end 206 spaced from the first end 204. The handling apparatus 200 further comprises a movable knock-out rod 208 having an end portion 210 insertable in the sleeve 202. A piston 212 is releasably attached to the end portion 210 of the knock-out rod 208. The piston 212 is configured to sealably engage the open end portion 121 of the container 120 when inserted therein. A vacuum port 214 is provided in the sleeve 202.

A first seal 216 is provided at the first end 204 of the sleeve 202. The first seal 216 is configured to sealing engagement with the sidewall 122 of the container 120. The first seal 216 may be any of various seals known in the mechanical arts, including, for example, an O-ring seal or an inflatable seal. A second seal 218 is provided at an opposing end 206 of the sleeve 202. The second seal 218 is configured to sealing engagement with the knock-out rod 208

In operation, a tub 110 containing a tray 40 of containers 120 is moved into position in a filling machine. Filling tubes are inserted into the containers 120 filling them to the prescribed level. Pistons 212 are applied to the ends of the knockout rods 208. One or preferably a plurality of first embodiment handling apparatuses 200 move over a corresponding plurality of containers 120. The apparatuses 200 move relative to the containers 120 such that the open end 121 of the containers 120 move within the open first end 204 of the sleeve 202, with the first seal 216 moving into sealing engagement with the sidewall 122 of the container 120. The first seal 216 cooperates with the second seal 218 to form an airtight seal of an interior of the sleeve 202 from the exterior. A vacuum is then applied via vacuum port 214, and the knock-out rod 208 advanced within the sleeve 202 such that the piston 212 is moved into position within the container 120. As the vacuum is released and the interior of the sleeve 202 is exposed to atmospheric pressure, the atmospheric pressure drives the piston 212 out of engagement with the end portion 210 of the knock-out rod 208 and into a final sealing position within the opening 121 of the container 120. If desired, the knock-out rod 208 may be used to drive the container 120 out of engagement with first seal 216.

Figure 18:
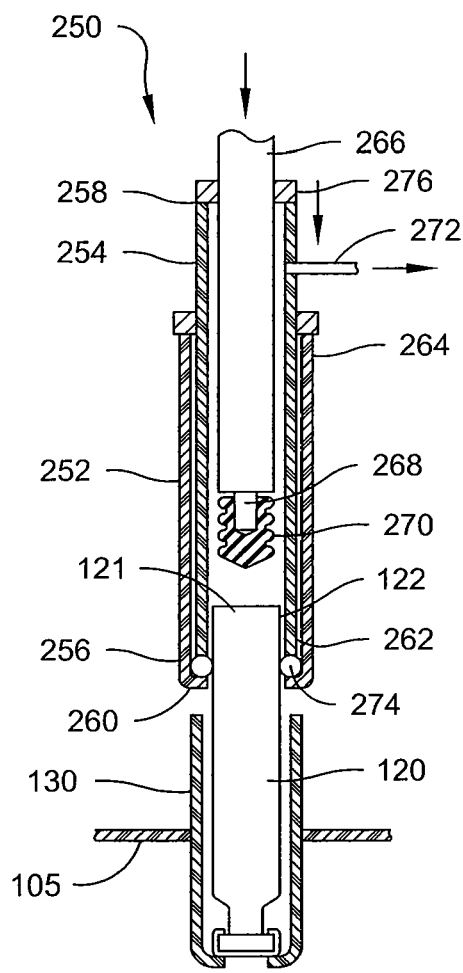
FIG. 18 is a side partial cross-sectional view of a second embodiment of a flangeless container handling apparatus in accordance with the present invention.

With reference now to FIG. 18, a second embodiment of a flangeless container handling apparatus 250 is generally similar to the first embodiment 200. The handling apparatus 250 is also for handling a flangeless container 120 during a filling operation. The flangeless container 120 has an open end portion 121 with an outer sidewall 122. However, the second embodiment 250 comprises two sleeves, an outer sleeve 252 and an inner sleeve 254. The outer sleeve 252 has a first end 256 and an opposing second end 258 spaced from the first end 256. The first end 256 has a radially inwardly extending lip 260. The inner sleeve 254 has a first end 262 and an opposing second end 264 spaced from the first end 262. The first end 262 of the inner sleeve 254 is in the outer sleeve 252. The outer and inner sleeves 252, 254 are axially movable relative to one another.

The handling apparatus 250 further comprises a movable knock-out rod 266 having an end portion 268 insertable in the inner sleeve 254. A piston 270 is releasably attached to the end portion 268 of the knock-out rod 266. The piston 270 is configured to sealably engage the open end portion 121 of the container 120 when inserted therein. A vacuum port 272 is provided in the inner sleeve 254.

A first compression seal 274 is provided at the first end 262 of the inner sleeve 254. The first compression seal is configured to sealably engage or disengage the outer sidewall 122 of the container 120 and the lip 260 of the outer sleeve 252 in response to an axial movement of the inner and outer sleeves 254, 252 relative to one another. A second seal 276 is provided at the second end 258 of the inner sleeve 254. The second seal 276 is configured to sealably engage the knock-out rod 266. The first seal 274 cooperates with the second seal 276 to form an airtight seal of an interior of the inner sleeve 254 when a vacuum is applied to the vacuum port 272.

Operation of the second embodiment of the handling apparatus 250 is thus generally similar to the operation of the first embodiment of the handling apparatus 200 described above. Containers 120 are filled by filling tubes (not shown) and pistons 270 are placed on the ends of the knockout rods 266. That is, the inner and outer sleeves 254, 252 move into position over open end 121 of container 120. Inner and outer sleeves 254, 252 move relative to one another to compress the first compressive seal 274 and engage the first compressive seal 274 with outer sidewall 122 of the container 120 and the lip 260 of the outer sleeve 252. A vacuum is applied via a vacuum port 272. The knock-out rod 266 is advanced, inserting piston 270 into the open end 121 of container 120. With the piston 270 inserted, the vacuum may be released, and differential pressure across the piston 270 tends to drive the piston 270 from the end-portion 268 of the knock-out rod 266.

Figure 19:
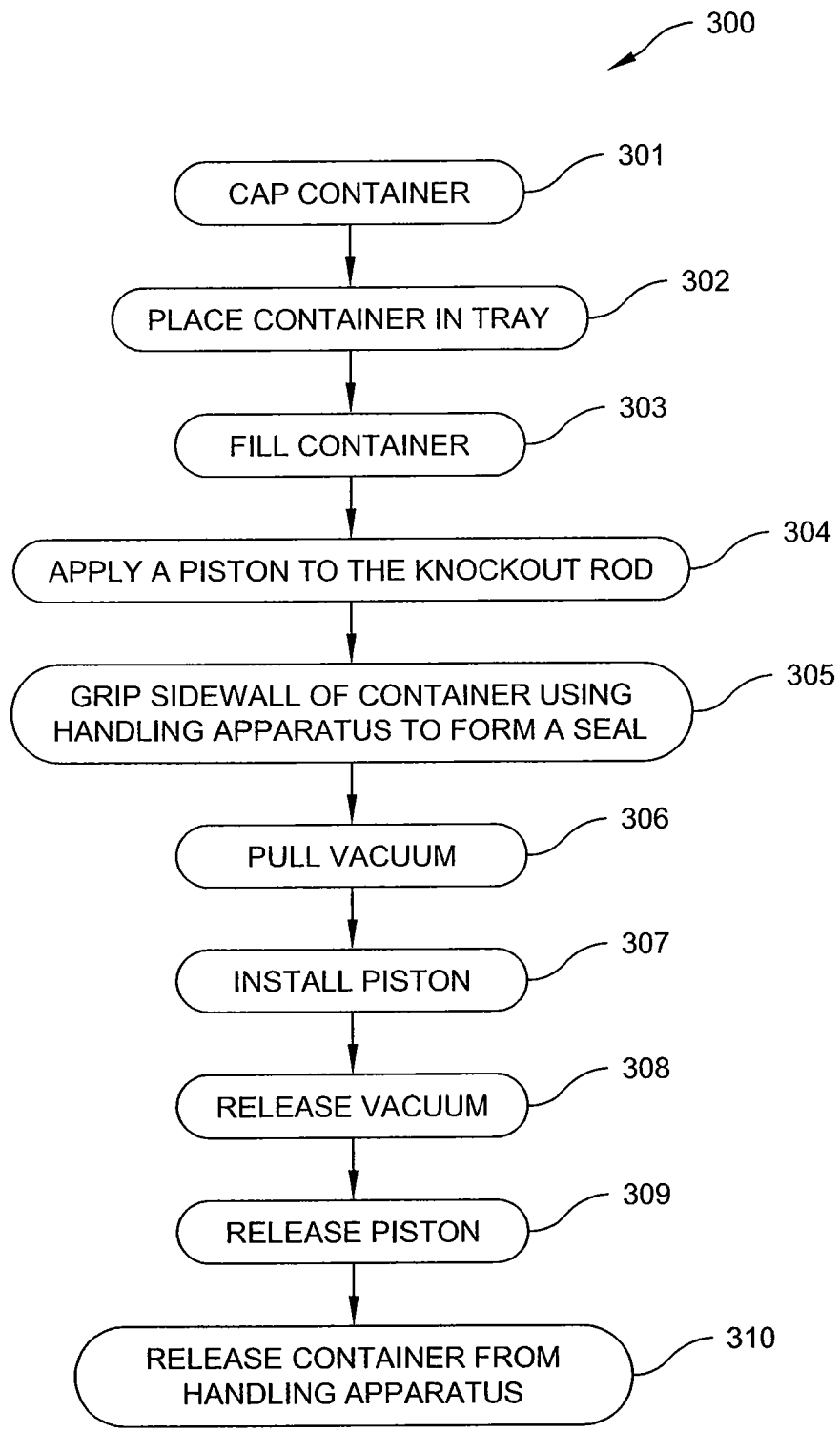
FIG. 19 is a flow chart illustrating steps comprising a first method of filling a flangeless container in accordance with the present invention.

In yet a fourth aspect, the invention is directed to methods of filling flangeless containers. With reference now to FIG. 19, steps of a first method 300 for filling flangeless containers are illustrated. In a first step 301, the container 120 is capped using a cap element (not shown) conventionally used with pre-filled drug containers. In a second step 302, the container 120 is installed in a tray 100. In a third step 303, the container 120 is filled. The container 120 may be removed from the tray 100 for filling, or filled while still in the tray 100. In a fourth step 304, a piston 212, 270 is applied to the knockout rod 208, 266. In a fifth step 305, the tray 100 is moved into position relative to a handling apparatus of the type disclosed herein, and the handling apparatus grips a side wall 122 of the container 120, forming a seal. In a sixth step, a vacuum is applied such that the open end 121 of the container 120 is exposed to vacuum conditions. In a seventh step 306, the piston 212, 270 is inserted into the container 120. In eighth and ninth steps 307, 308, respectively, the vacuum is released and the piston 212, 270 is disengaged from the knock-out rod 208, 266 carrying the piston. In a tenth step 309, the container 120 is released from the handling apparatus.

Figure 20:
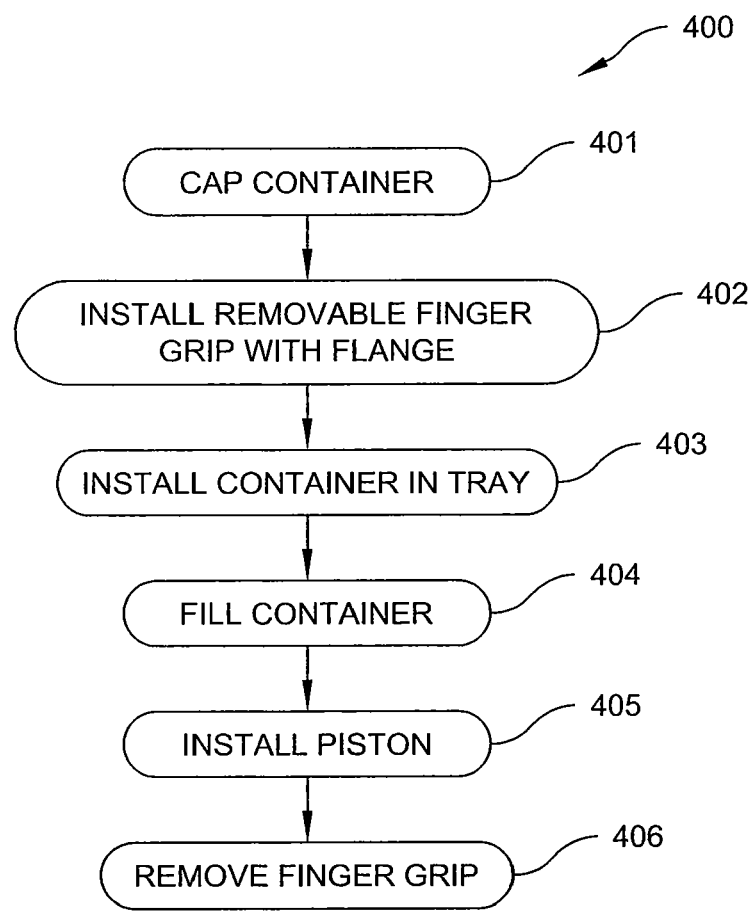
FIG. 20 is a flow chart illustrating steps comprising a second method of filling a flangeless container in accordance with the present invention.

With reference now to FIG. 20, steps of a second method 400 for filling flangeless containers are shown. In a first step 401, the container 120 is capped using a conventional cap element typically used with pre-filled drug containers. In a second step 402, a removable, temporary finger grip with a flange of the type disclosed herein above is attached to the container 120. In a third step 403, the container 120 is installed in a tray. In a fourth step 404, the container 120 is filled in a conventional manner. In a fifth step 405, a piston is installed in the container 120 in a conventional manner. In a sixth step 406, the temporary finger grip is removed from the container 120.

We claim:

1. A finger grip for a flangeless container having a generally cylindrical cross-sectional shape and an open end portion having an outside surface, the finger grip comprising:
   a skirt having a generally cylindrical cross-sectional shape, a continuous inner surface extending over the entire longitudinal and circumferential extent of the skirt and a continuous outer surface extending over the entire longitudinal and circumferential extent of the skirt, the skirt removably attachable to the open end portion of the container; and
   a lip extending radially outwardly from the skirt,
   wherein the skirt circumscribes the outside surface of the open end portion of the container and is removably attached to the outside surface by a frictional fit extending over the entire longitudinal and circumferential extent of the skirt, and
   wherein the skirt is formed as a single unitary structure separable at an area with a weakened cross-section extending longitudinally in the outside surface of the skirt.

2. A finger grip for a flangeless container having a generally cylindrical cross-sectional shape and an open end portion terminating with an annular surface entirely in a plane perpendicular to a longitudinal axis of the container, the annular surface of the container having a radial extent, the finger grip comprising:
   a skirt having an arcuate cross-sectional shape and a longitudinal extent having a first end and a second end spaced from the first end, the second end removably attachable to the open end portion of the container; and
   a lip extending radially outwardly from the first end of the longitudinal extent of the skirt,
   wherein the second end of the longitudinal extent of the skirt forms a continuous first annular surface having a radial extent substantially the same as the radial extent of the annular surface of the container, the continuous first annular surface entirely in the plane perpendicular to the longitudinal axis of the container and attachable to the annular surface of the container by a releasable adhesive.

3. A finger grip for a flangeless container having a generally cylindrical cross-sectional shape and an open end portion having an outside surface, the finger grip comprising:
   a skirt having a generally elliptical cross-sectional shape and a longitudinal extent, the skirt removably attachable to the open end portion of the container,
   wherein the skirt comprises an outer sleeve with a first elliptical cross-section and an inner sleeve with a second elliptical cross-section in the outer sleeve and a lip comprising a first lip portion extending radially outwardly directly from the outer sleeve and a second lip portion extending radially outwardly directly from the inner sleeve, wherein a rotational movement of the inner and outer sleeves relative to one another about a longitudinal axis of the skirt causes the inner surface of the inner sleeve to engage or disengage the outside surface of the open end portion of the container.

4. A finger grip for a flangeless container having a generally cylindrical cross-sectional shape and an open end portion, the finger grip comprising:
   an outer sleeve having a bore with a tapered radially inwardly facing surface;
   a lip extending radially outwardly directly from the outer sleeve;
   a split sleeve in the bore of the outer sleeve, the split sleeve having a tapered radially outwardly facing surface operatively coupled to the tapered radially inwardly facing surface of the outer sleeve and a split sleeve bore removably attachable to the open end portion of the container,
   wherein movement of the outer sleeve in a first axial direction relative to the split sleeve tightens engagement of the inner sleeve with the container and movement of the outer sleeve in a second axial direction opposite the first axial direction relative to the split sleeve loosens engagement of the split sleeve with the container when the container is in the bore of the split sleeve.

* * * * *